US007951278B2

(12) United States Patent
Santiago et al.

(10) Patent No.: US 7,951,278 B2
(45) Date of Patent: May 31, 2011

(54) METHOD OF DETECTING DIRECTLY UNDETECTABLE ANALYTES USING DIRECTLY DETECTABLE SPACER MOLECULES

(75) Inventors: Juan G. Santiago, Stanford, CA (US); Tarun Khurana, Stanford, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 793 days.

(21) Appl. No.: 11/880,479

(22) Filed: Jul. 20, 2007

(65) Prior Publication Data

US 2008/0197019 A1 Aug. 21, 2008

Related U.S. Application Data

(60) Provisional application No. 60/832,332, filed on Jul. 20, 2006.

(51) Int. Cl.
*G01N 27/26* (2006.01)
(52) U.S. Cl. .................................. 204/549; 204/645
(58) Field of Classification Search ................. 204/549, 204/645
See application file for complete search history.

(56) References Cited

U.S. PATENT DOCUMENTS 3,948,753 A * 4/1976 Arlinger ........................ 204/601
2005/0121324 A1* 6/2005 Park et al. ..................... 204/451
2005/0133370 A1 6/2005 Park et al.

OTHER PUBLICATIONS

Nagoyova, Iveta et al. "Discrete Spacers for Photometric Characterization of Humic Acids Separated by Capillary Isotachophoresis." 2001. Journal of Chromatography A, pp. 191-200.
Oerlemans, F. et al. "Isotachophoresis of Urinary Purines and Pyrimidines: The Use of Spacers and Enzymes for Identification." 1981. Journal of Chromatography 225, pp. 369-379.
Gross, Larry et al. "Indirect Fluorometric Detection of Cations in Capillary Zone Electrophoresis." 1990. American Chemical Society, pp. 427-431.
Schafer-Nielsen et al. Separation of Macromolecules in Isotachophoresis Systems Involving Single or Multiple Counterions, Journal of Biochemical and Biophysical Methods, 3 (1980) 97-128.

* cited by examiner

*Primary Examiner* — Alexa D Neckel
*Assistant Examiner* — Jennifer Dieterle
(74) *Attorney, Agent, or Firm* — Lumen Patent Firm

(57) ABSTRACT

The present invention provides a method of indirectly detecting at least one directly undetectable analyte of interest. According to the method, a leading electrolyte and a trailing electrolyte are provided. In addition, a mixture of the at least one directly undetectable analyte and at least two directly detectable spacer molecules is provided. The directly detectable spacer molecules and the directly undetectable analyte are then concentrated and separated into zones using isotachophoresis. A displacement between the zones of directly detectable spacer molecules is then used to determine the presence of the directly undetectable analyte.

18 Claims, 6 Drawing Sheets

METHOD OF DETECTING DIRECTLY UNDETECTABLE ANALYTES USING DIRECTLY DETECTABLE SPACER MOLECULES

CROSS-REFERENCE TO RELATED APPLICATIONS

This application claims priority from U.S. Provisional Patent Application No. 60/832,332, filed Jul. 20, 2006, which is incorporated herein by reference.

FEDERALLY-SPONSORED RESEARCH OR DEVELOPMENT

The present invention was supported in part by grant No. HV028183 from the National Institutes of Health (NIH). The U.S. Government has certain rights in the invention.

FIELD OF THE INVENTION

The present invention relates generally to analyte detection. More particularly, the present invention relates to indirect detection of directly undetectable analytes using directly detectable spacer molecules.

BACKGROUND

Direct detection of analytes has many drawbacks, as many analytes are not directly detectable by current techniques. Indirect methods, such as fluorescent or radioactive labeling, are possible, but also have drawbacks. For example, not all analytes can be labeled efficiently, and radioactivity presents safety and licensing concerns.

Other indirect detection methods using either fluorescence or UV-absorbance offer alternate solutions to fluorescent or radioactive labeling. These methods employ strongly UV absorbing/fluorescent markers which are added to the entire background buffer to yield a background signal that is uniform in the absence of analyte ions. Non-fluorescent/non-UV absorbing analyte species are then injected into a separation channel and separated via capillary zone electrophoresis (CZE). As analytes migrate, separate, and disperse, they locally displace the background marker as per the requirements of electroneutrality and current conservation. The displacement of detectable marker ions by undetected analyte ions leads to a reduction in the background signal at the analyte peak location. This local decrease in the background signal is an indirect detection of the analyte zone. These traditional indirect detection methods, however, offer no pre-concentration ability, and are therefore usually limited to analyte concentrations above about 0.1 mM. This fairly low sensitivity technique is also susceptible to false positive identifications due to the presence of so-called false system peaks arising in part from disturbances in the background ion distribution created by sample injection. Changes in the background signal due to Joule heating or unstable illumination can also cause false peaks in these indirect detection techniques. Accordingly, there is a need in the art to develop new, more sensitive methods of indirectly detecting analytes that have lower false positive rates.

SUMMARY OF THE INVENTION

The present invention provides such a method. Specifically, the present invention provides a method of indirectly detecting at least one directly undetectable analyte of interest. According to the method, a leading electrolyte and a trailing electrolyte are provided. In addition, a mixture of the at least one directly undetectable analyte and at least two directly detectable spacer molecules is provided. The directly detectable spacer molecules and the directly undetectable analyte are then concentrated and separated into zones using isotachophoresis. A displacement between the zones of directly detectable spacer molecules is then used to determine the presence of the directly undetectable analyte.

Preferably, the spacer molecules, but not the analyte, are directly detectable by at least one of fluorescence, electrochemical means, UV absorbance, thermo-optical absorbance, or radiochemical means. Alternatively, or in addition, the directly detectable spacer molecules may be labeled polymers, including but not limited to labeled DNA, RNA or dextran.

In a preferred embodiment, the method also includes bounding the mobility of the at least one directly undetectable analyte of interest. This is done by determining the mobility of the zones of the directly detectable spacer molecules that are on either side of the zone of the analyte of interest. The shapes of the neighboring zones may also be taken into account. Preferably, this bounding includes determining at least one of a continuous, analog, discrete, or digital estimate of the mobility of the analyte of interest. In addition to determining the mobility of the analyte of interest, the initial concentration of the directly undetectable analyte of interest may be determined by measuring the distance between the neighboring zones.

In a preferred embodiment, the identity of the directly detectable spacer molecules is encoded. This may be accomplished in many ways, such as encoding the signal intensity of the spacer molecules, and/or using different fluorescence absorption and/or emission wavelengths for different spacer molecules.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
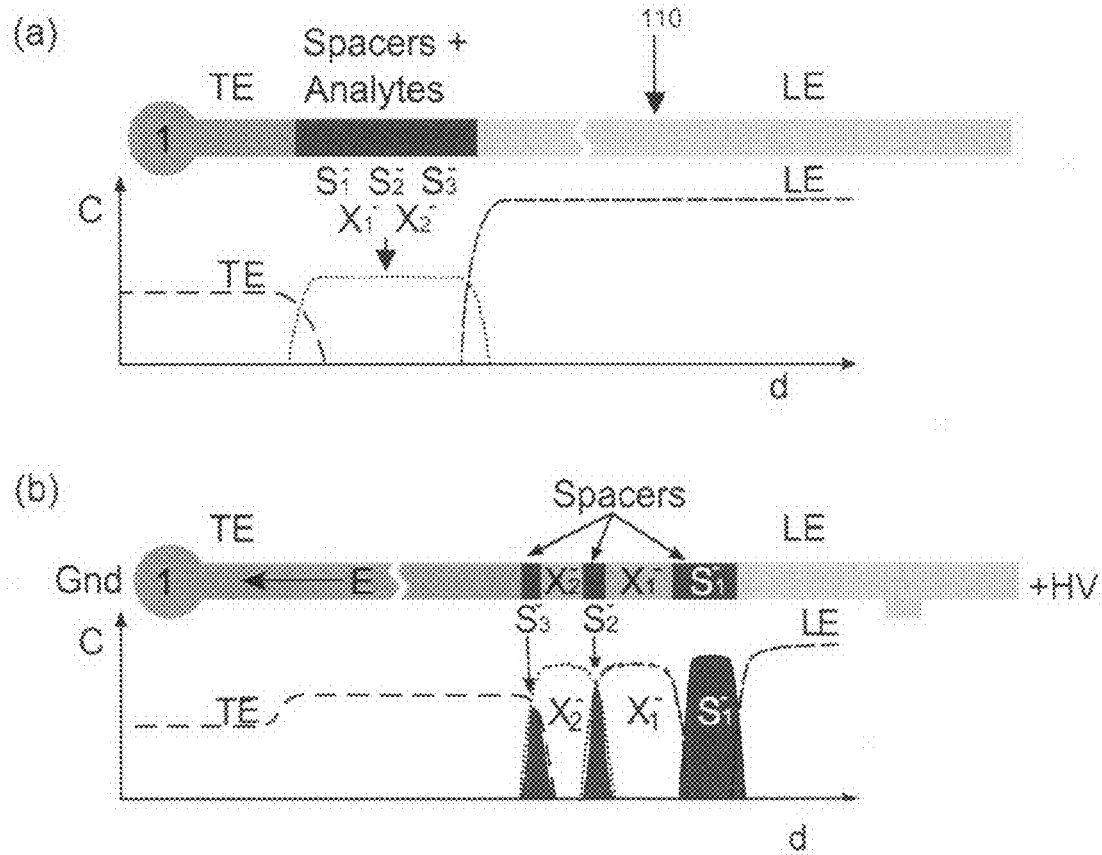
FIG. 1 shows a schematic of production of spacer and analyte zones according to the method of the present invention.

The present invention provides a method of indirectly detecting at least one directly undetectable (i.e. otherwise undetectable) analyte of interest. By "directly undetectable" it is meant that one of ordinary skill in the art would be unable to detect the analyte using techniques known in the art. For example, electrochemical detection requires electrochemical reactions to occur between the analyte of interest and electrolytes. In this case, "undetectable" may mean negligible rates of such reactions or the presence of a reaction, but a signal to noise ratio (SNR) that is too low for detection. Thus, spacers would be chosen that react well in the presence of electrolytes. In the case of UV or thermo-optical absorbance, the SNR may again be too low for detection, e.g. due to low absorption cross-section at the wavelength of interest. That is, the analyte physically doesn't absorb well. Thus, spacers would be chosen with particularly high absorbance properties. In the case of radiochemical or fluorescence methods, analytes can be non-(or negligibly) radioactive or fluorescent (so low SNR). In this case, spacers would be chosen that are purposely radioactive or have desirable fluorescent properties. Other examples are also possible, and the cited examples should not be taken to be limiting. Preferably, a directly undetectable analyte is defined has having a SNR in a given detection scheme of less than about 3.

Directly detectable spacers may be molecules or polymers that intrinsically have, e.g., one of the above-desired properties, or they may be modified to have a desired property. In a preferred example, the spacer molecules are fluorescent molecules or fluorescently labeled polymers, such as DNA, RNA, or dextran. Preferably, at least three directly detectable spacer molecules are provided, concentrated, and detected according to the present invention.

Any directly undetectable analyte may be detected according to the present invention. Examples include, but are not limited to amino acids, nucleotides, oligonucleotides, metabolites, food additives, peptides, drug constituents, toxins, pathogens, heavy metals, heavy-meal-ligand complexes, viruses, single-celled organisms (including bacteria), hormones, and biological and chemical weapons. Preferably, the method of the present invention has a sensitivity of detection of at least 500 nM, more preferably 250 nM, even more preferably 100 nM, and most preferably 10 nM.

According to the present invention, the directly detectable spacer molecules and the at least one analyte are mixed together, a leading electrolyte and trailing electrolyte are provided, and the spacer molecules and analyte are concentrated into zones using isotachophoresis (ITP). Any leading electrolyte and trailing electrolyte traditionally used with ITP by one of ordinary skill in the art may be used according to the present invention. Preferably, the leading electrolyte is in the range of about 5-350 mM with a pH in the range of about 4 and 11. The leading electrolyte may be, e.g. Tris-HCl. However, any electrolyte with a higher electrophoretic mobility co-ion than all the spacers/analytes may be used. Preferably, the trailing electrolyte is in the range of about 5-50 mM sodium tetraphenylborate. However, any buffer with a lower electrophoretic mobility co-ion than all of the spacers/analytes may be used. Preferably, the spacer molecule/analyte mix is injected into a capillary system, such as a chip-based system. This injection may be driven electrokinetically or using pressure driven flow.

FIG. 1 shows an example of a schematic of the method according to the present invention. In FIGS. 1(a) and (b), the top section of the figure shows a capillary and the bottom section of the figure shows a trace of signal intensity versus distance of the items in the capillary. In this example, capillary 110 is initially filled with leading electrolyte LE. Next, a finite injection volume of a mixture of analytes $X_1^-$ and $X_2^-$ and spacer molecules $S_1^-$, $S_2^-$, and $S_3^-$ is loaded into well 1 and injected into capillary 110. Well 1 is then preferably emptied, rinsed, and loaded with trailing electrolyte TE (a). As can be seen in detail from the bottom section of FIG. 1(a), the spacers and analytes redistribute themselves in respective zones between LE and TE in order of reducing effective mobility. As shown in FIG. 1(b), an electric field is then applied (+HV is positive high voltage and Gnd is ground) to capillary 110. The exact voltage will depend on the capillary diameter, length and LE concentration and dispersion effects. The arrow labeled E shows the direction of flow of electrons. The presence of the electric field causes the spacers to segregate into zones, as shown by the arrows. These zones are displaced by analytes $X_1^-$ and $X_2^-$, which are seen as gaps of signal intensity between the spacers.

Figure 2:
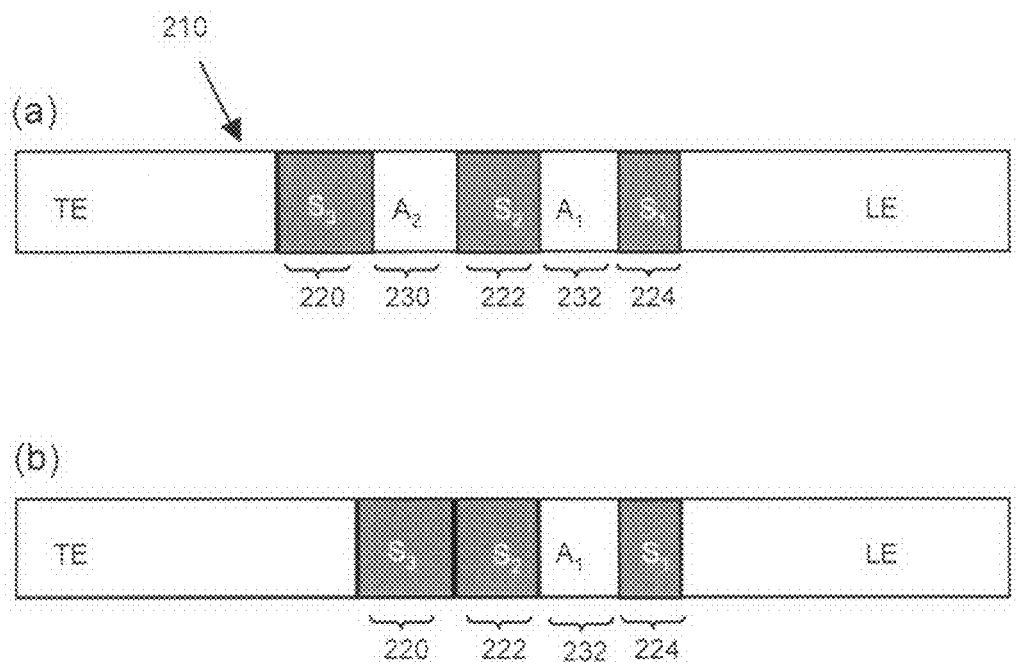
FIG. 2 shows a schematic of detection of analytes according to the method of the present invention.

This concept is further illustrated in FIG. 2. FIG. 2(a) shows a schematic of a capillary with a leading electrolyte (LE), two directly undetectable analytes ($A_1$ and $A_2$), three directly detectable spacers ($S_1$, $S_2$ and $S_3$) and a trailing electrolyte (TE) that have undergone ITP according to the method of the present invention. Directly detectable spacers $S_1$, $S_2$ and $S_3$ have been separated into three zones. Zone 220 contains $S_3$, zone 222 contains $S_2$, and zone 224 contains $S_3$. Similarly, directly undetectable analytes $A_1$ and $A_2$ have been separated into zones 230 and 232, respectively. In contrast, FIG. 2(b) shows a schematic of the same experiment conducted in the absence of $A_2$. In this case, spacer zones 220 and 222 merge together. Thus, the presence of analyte $A_2$ can be detected by a displacement of spacer zones 220 and 222.

In a preferred embodiment, the method of the present invention further includes bounding the mobility of the at least one directly undetectable analyte of interest by determining the mobility of the zones of directly detectable spacer molecules that are on either side of the zone of the directly undetectable analyte. For example, referring to FIG. 2(a), the upper boundary of mobility of $A_2$ may be determined by analyzing the mobility of zone 222, and the lower boundary of mobility of $A_2$ may be determined by analyzing the mobility of zone of 220. The analysis of mobility may be a continuous, analog, discrete, or digital estimate of mobility. Bounding may further comprise analyzing the shape of the neighboring zones. The diffusion/electromigration length scale at the interface of the spacer and the sample is a function of the difference of the mobility of these two species.

$$\frac{l_d}{w} = f(v_{spacer} - v_{sample})$$

Using the characteristic diffusion length scales at the two edges of the sample band and the mobilities of the spacers on either ends, the correct mobility of the unknown sample species can be estimated.

In another preferred embodiment, the initial concentration of the directly undetectable analyte of interest is determined by measuring the distance between directly detectable spacer zones that are adjacent to the zone containing the analyte. If the analyte zones obey the Kohlrasch regulating function (KRF) condition, the initial concentration is a linear function of the spacer gap width. For relatively thin interfaces (~few microns thick) between spacers and analytes, the distance between adjacent spacers is simply proportional to initial analyte concentration as per eq 1:

$$L_{X_i} = \frac{C_{0,X_i} L_0}{C_{X_i}} \quad (1)$$

where $L_{X_i}$ is the length of each analyte zone, $L_0$ is the length of the injected plug length, $C_{0,X_i}$ is the initial concentration of analyte $X_i$, and $C_{X_i}$ is its final concentration given by eq 2:

$$C_{X_i} = C_L \left(\frac{v_{X_i}}{v_L}\right)\left(\frac{v_L + v_A}{v_{X_i} + v_A}\right) \quad (2)$$

where $C_i$ and $v_i$ are the concentration and the mobility of species i, at axial location x in the capillary, for leading ion (L), trailing ion (T), $i^{th}$ sample ion ($X_i$) and counterion (A).

The method of the present invention may further include encoding the identity of the at least two directly detectable spacer molecules. This can be accomplished in many ways. In one embodiment, the encoding is accomplished by encoding the signal intensity of the spacer molecules. In one example of this embodiment, the ITP is operated in spike mode for the spacer molecules, but not for the analytes of interest. In another example, different starting concentrations of adjacent spacer molecules may be used. In yet another example, adjacent spacer molecules have different levels of signal, such as different quantum yields. In another embodiment, encoding is accomplished using spacer molecules with different fluorescence absorption, emission, or absorption and emission wavelengths.

EXAMPLES

Materials

We used 350 mM Tris-HCl (titrated to pH 10.2 with sodium hydroxide) as the leading electrolyte and 50 mM sodium tetraphenylborate as the trailing electrolyte. We prepared 50 mM stock solutions of Tris-serine and Tris-phenylalanine to be used as sample analytes. These amino acids have respective $pK_a$ values of 9.3 and 9.26. The amino acids, leading and trailing electrolyte reagents were obtained from Sigma Aldrich (St. Louis, Mo.). The fluorescent spacers were Oregon Green carboxylic acid, Fluorescein and Bodipy, and were obtained from Molecular Probes (Eugene, Oreg.). We prepared 10 μM concentration stock solutions of these fluorescent spacers and diluted their final concentration to 50 nM in the analyte-spacer mixture. All solutions were prepared using ultra-filtered deionized water (DIUF) obtained from Fischer Scientific (Fair Lawn, N.J.). The experiments were performed on standard, commercially available borosilicate microfluidic chips with "simple cross" geometry (Micralyne, Alberta, Canada) with wet-etched channels 50 μm wide and 20 μm deep.

Assay Protocol

The chip was first filled with LE. Well 1 was then emptied (using a pipette connected to vacuum line). rinsed 2-3 times (by repeatedly filling with deionized water and emptying), and filled with the solution containing the analytes and spacers. A finite plug of spacer-analyte mixture was injected using pressure driven flow by applying a vacuum on well 4 for ~10 s (we used an inverted pipette tip with an O-ring at the end to form an imperfect seal between the vacuum line and the chip). We achieved injection lengths of 6±0.2 mm by real-time monitoring of the injection front with the CCD camera. Well 1 was then emptied again and filled with the trailing electrolyte. Once the chip was loaded, high voltage (~1200 V) was applied across wells 3 and 1. The electrophoretic species then migrated under the influence of electric field and segregated into their respective ITP zones.

Measurement of Temporal Resolution

Figure 3:
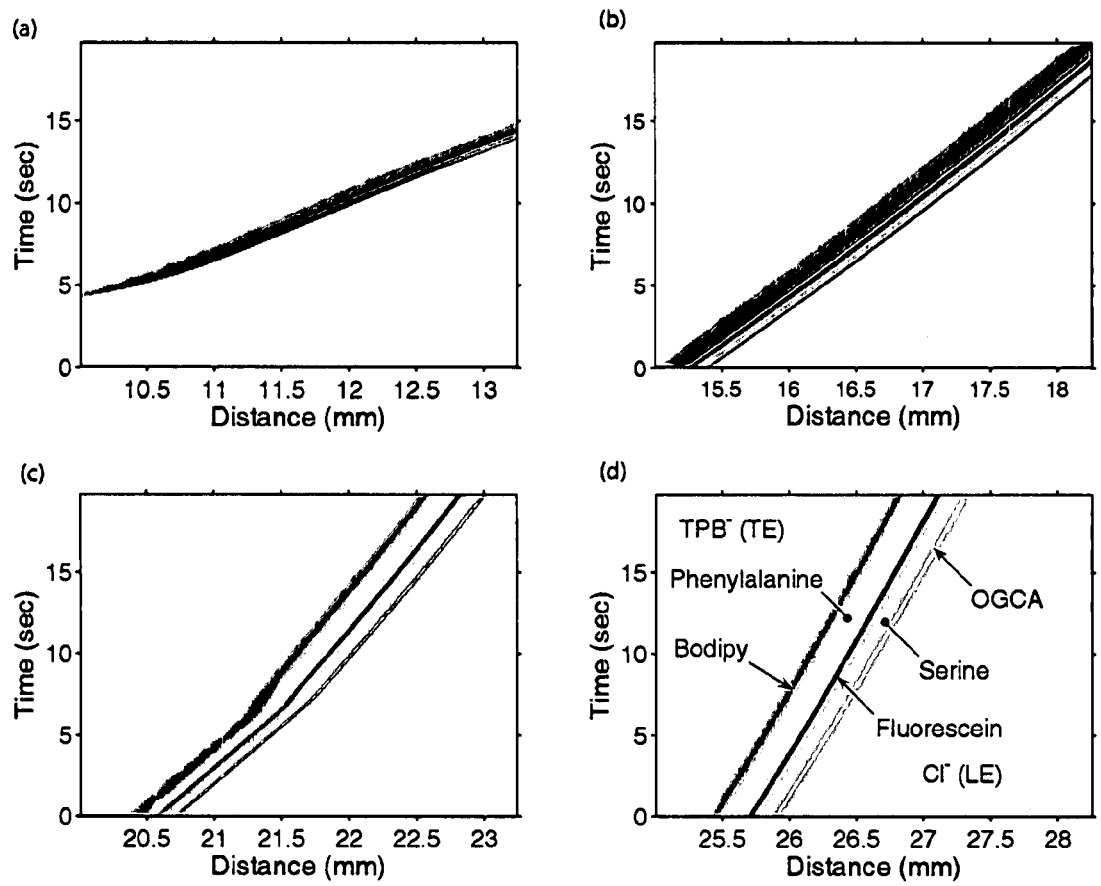
FIG. 3 shows an example of measurements of fluorescence versus time according to the present invention.

FIG. 3 shows measurements of spacer fluorescence intensity versus time and distance along the 50 μm wide (by 20 μm deep) separation channel. The intensity scale is inverted so a dark streak denotes high intensity. The spacer bands are initially detectable as a faint, single peak at $x \leq 10.5$ mm (a). The spacers then concentrate and separate in a series of phases into three spacer peaks (b-c). At $x \geq 21.5$ mm, the peaks reach a steady state velocity (constant slope) and spacing (d). The three diagonal stripes then clearly describe the location and constant velocity motion of the three spacer peaks. The presence of two unlabeled analytes (phenylanaline and serine) is signaled by two "gaps" between spacer bands.

Effect of Analyte Presence on Spacer Mobility

Figure 4:
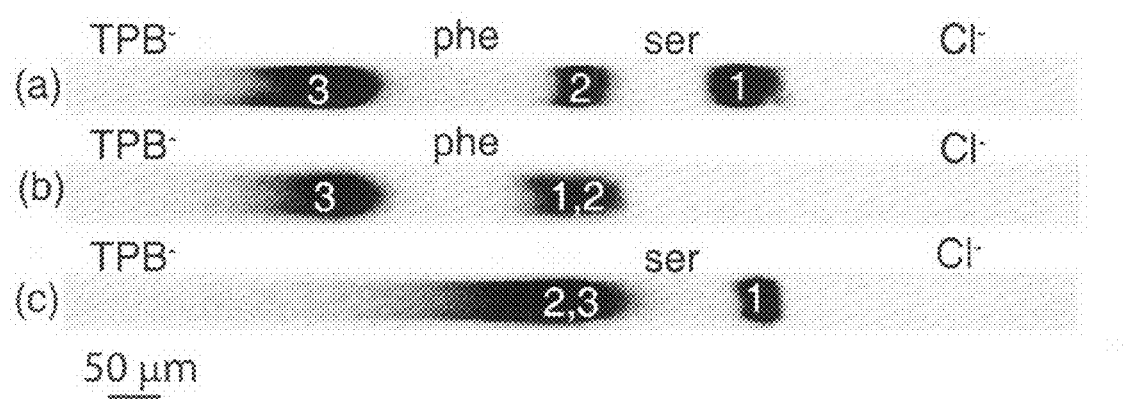
FIG. 4 shows an example of images of separated spacers according to the method of the present invention using different combinations of analytes.

FIG. 4 shows raw inverted-intensity images of fluorescent spacer peaks in a 50 μm wide (by 20 μm deep) microchannel, 25 mm downstream from the TE well. Shown are three high LE (350 mM Tris-HCl, pH 10.2) ITP-spacer experiments. In (a), both analytes phenylalanine (phe) and serine (ser) were present in the sample mixture. In (b), only phenylalanine was present and spacers 1 and 2 merged together; and in (c) only serine was present and spacers 2 and 3 merged. The initial amino acid concentrations were 10 mM. The injected plug length was 6 mm in all cases. Cl⁻ is chloride; TPB⁻ is tetraphenylborate; and spacers 1, 2, and 3 are respectively Oregon Green-carboxylic acid, Fluorescein, and Bodipy.

Effect of Analyte Concentration on Spacing between Adjacent Spacers

Figure 5:
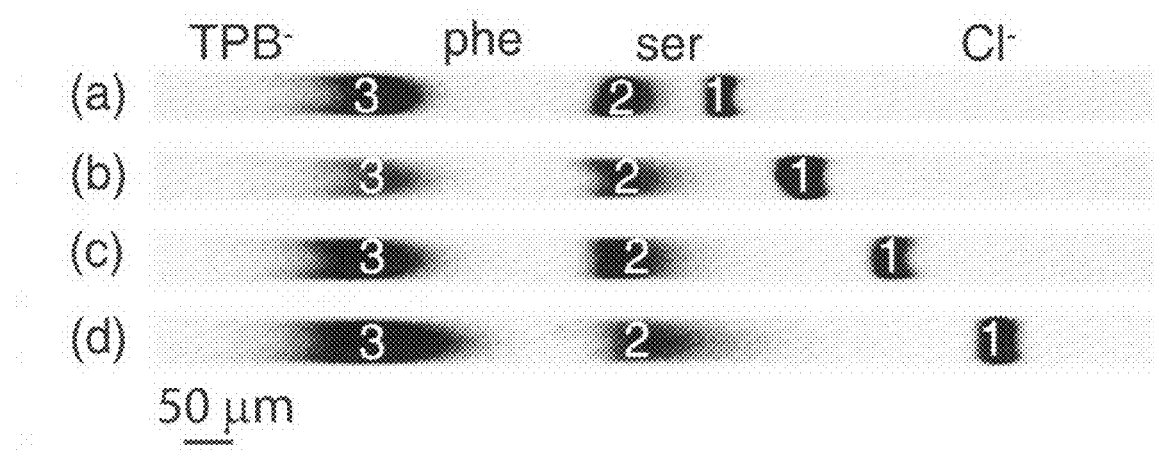
FIG. 5 shows an example of images of separated spacers according to the method of the present invention using different concentrations of analytes.

FIG. 5 shows raw inverted-intensity images of the fluorescent spacers inside the microchannel, 25 mm downstream from the injection point for high LE concentration experiments. Shown here are four cases, where the concentration of serine (ser) was increased linearly to give 5 mM (a), 10 mM (b), 15 mM (c) and 20 mM (d), showing the effect of change in concentration of an analyte on the spacing between the adjacent spacers. As expected, there is a linear increase in the gap width between spacers 1 and 2 as initial serine concentration is increased in equal increments. The concentration of phenylalanine (phe) was fixed at 10 mM and LE was 350 mM Tris-HCl, pH 10.2. The injected plug was 6 mm in all the cases. Again, Cl⁻ is chloride; TBP⁻ is tetraphenylborate; and spacers 1, 2, and 3 are respectively Oregon Green-carboxylic acid, Fluorescein, and Bodipy.

Spacer Identity Encoding Schemes

Figure 6:
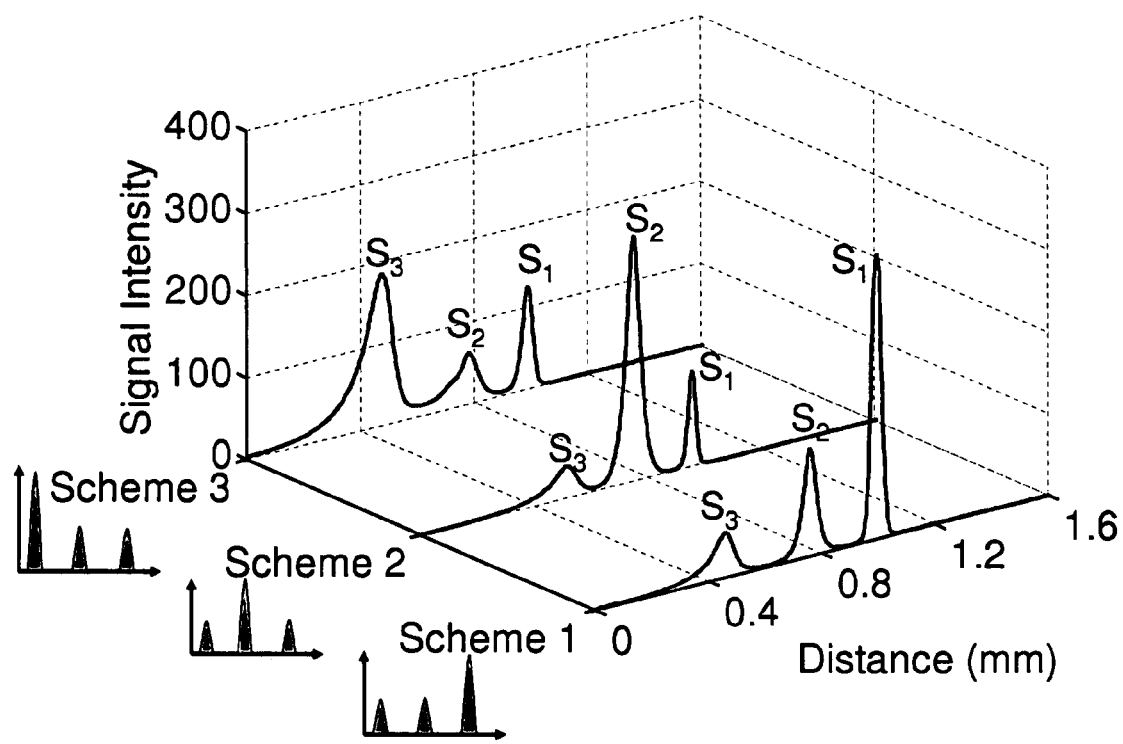
FIG. 6 shows an example of signal intensity coding of spacers according to the present invention.

FIG. 6 shows measurements of spacer signal intensity versus distance along the separation channel for three fluorescent spacer-encoding experiments. In this experiment, the initial concentration of one fluorescent spacer was spiked to 200 nM, while the other two spacer concentrations were fixed at 50 mM. Schemes 1, 2, and 3 are respectively high-low-low, low-high-low, and low-low-high encoding schemes with respect to signal intensity of spacers $S_1$, $S_2$ and $S_3$. The spiked spacer is readily identifiable in each case. LE was 350 mM Tris-HCl with pH 10.2. Analytes were 10 mM serine and phenylalanine, and TE was 50 mM sodium tetraphenylborate. The spacers $S_1$, $S_2$, and $S_3$ are Oregon Green carboxylic acid, Fluorescein and Bodipy, respectively. Here, ITP is in spike mode for fluorescent spacers and so final spacer concentration is an approximately linear function of its initial concentration.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of indirectly detecting at least one directly undetectable analyte of interest, comprising:
   a) providing a leading electrolyte and a trailing electrolyte;
   b) providing a mixture of said at least one directly undetectable analyte of interest and at least two directly detectable spacer molecules;

c) concentrating and separating said at least one directly undetectable analyte of interest and said at least two directly detectable spacer molecules into zones using isotachophoresis;

d) detecting a displacement between said zones of directly detectable spacer molecules, wherein detection of said displacement results in the indirect detection of said at least one directly undetectable analyte of interest.

2. The method as set forth in claim 1, wherein said at least one analyte is not directly detectable by fluorescence, electrochemical means, UV absorbance, thermo-optical absorbance, or radiochemical means.

3. The method as set forth in claim 1, wherein said at least two directly-detectable spacer molecules are detectable by fluorescence, electrochemical means, UV absorbance, thermo-optical absorbance, or radiochemical means.

4. The method as set forth in claim 1, wherein said at least two directly-detectable spacer molecules are labeled polymers.

5. The method as set forth in claim 1, further comprising determining the initial concentration of said at least one directly undetectable analyte of interest by measuring the distance between said zones of said directly detectable spacer molecules that are on either side of said at least one directly undetectable analyte of interest.

6. The method as set forth in claim 1, wherein said at least one analyte of interest is at least one of an amino acid, a nucleotide, an oligonucleotide, a metabolite, a food additive, a peptide, a drug constituent, a toxin, a pathogen, a heavy metal, a heavy-metal-ligand complex, a virus, a single celled organism, a hormone, a chemical weapon, or a biological weapon.

7. The method as set forth in claim 1, wherein said directly undetectable analyte of interest has a signal to noise ratio in a particular detection scheme of less than about 3.

8. The method as set forth in claim 1, comprising providing, concentrating, and detecting at least three directly-detectable spacer molecules.

9. The method as set forth in claim 1, further comprising injecting said analyte/spacer mixture, wherein said injecting is driven electrokinetically or using pressure driven flow.

10. The method as set forth in claim 1, further comprising bounding the mobility of said at least one directly undetectable analyte of interest by determining the mobility of said zones of said directly detectable spacer molecules that are on either side of said zone of said at least one directly undetectable analyte of interest.

11. The method as set forth in claim 10, wherein said bounding comprises determining at least one of a continuous, analog, discrete, or digital estimate of mobility of said directly undetectable analyte of interest.

12. The method as set forth in claim 10, wherein said bounding further comprises analyzing the shape of said zones of said directly detectable spacer molecules that are on either side of said at least one directly undetectable analyte of interest.

13. The method as set forth in claim 1, further comprising encoding the identity of said at least two directly-detectable spacer molecules.

14. The method as set forth in claim 13, wherein said encoding comprises utilizing different fluorescence absorption wavelengths, different fluorescence emission wavelengths, or different fluorescence absorption and emission wavelengths in said at least two directly-detectable spacer molecules.

15. The method as set forth in claim 13, wherein said encoding comprises encoding signal intensity of said at least two directly detectable spacer molecules.

16. The method as set forth in claim 15, wherein said encoding of said signal intensity comprises operating said isotachophoresis in spike mode for said at least two directly-detectable spacer molecules and not for said at least one analyte of interest.

17. The method as set forth in claim 15, wherein said encoding of said signal intensity comprises using different starting concentrations of adjacent molecules of said at least two directly-detectable spacer molecules.

18. The method as set forth in claim 15, wherein said encoding of said signal intensity comprises using adjacent directly-detectable spacer molecules having different quantum yields.

* * * * *

UNITED STATES PATENT AND TRADEMARK OFFICE
CERTIFICATE OF CORRECTION

PATENT NO. : 7,951,278 B2  
APPLICATION NO. : 11/880479  
DATED : May 31, 2011  
INVENTOR(S) : Juan G. Santiago et al.

Page 1 of 1

It is certified that error appears in the above-identified patent and that said Letters Patent is hereby corrected as shown below:

In the Specification

In Column 1, starting at line 16 please correct the following statement from:

The present invention was supported in part by grant number HV028183 from the National Institutes of Health (NIH). The U.S. Government has certain rights in the invention.

to

The invention was made with Government support under contract HV028183 awarded by the National Institutes of Health. The U.S. Government has certain rights in the invention.

Signed and Sealed this
Thirty-first Day of March, 2015

Michelle K. Lee
*Director of the United States Patent and Trademark Office*